United States Patent [19]

Warren et al.

[11] Patent Number: 4,474,891

[45] Date of Patent: Oct. 2, 1984

[54] MINI-IODINATED POLYPEPTIDE HORMONE TRACER AND METHOD FOR ITS USE

[76] Inventors: Michelle P. Warren, 134 E. 73rd St., New York, N.Y. 10021; Elsie C. Ewen, 73 Stelling Ave., Maywood, N.J. 07607

[21] Appl. No.: 387,120

[22] Filed: Jun. 10, 1982

[51] Int. Cl.³ .................... G01N 33/56; G01N 33/58; A61K 43/00
[52] U.S. Cl. .................... 436/500; 436/505; 436/510; 436/540; 436/542; 436/545; 436/804; 436/814; 436/817
[58] Field of Search .................... 424/1, 1.5; 436/504, 436/545, 542, 804, 540, 500, 505

[56] References Cited

U.S. PATENT DOCUMENTS

| | | | |
|---|---|---|---|
| 4,094,963 | 6/1978 | Saxena | 436/504 |
| 4,202,874 | 5/1980 | Akerkar et al. | 436/804 |
| 4,277,393 | 7/1981 | Sakakibara et al. | 424/1.5 |
| 4,297,494 | 10/1981 | Groman et al. | 424/1.5 |
| 4,331,646 | 5/1982 | Delaage | 424/1 |

OTHER PUBLICATIONS

Dobracheva et al., Chemical Abstracts, vol. 90 (1979) #2676g.
Ketelslegers et al., J. Clinical Endocrinol Metab. 39: 1159–1162 (1974).
Pinto et al., Clinica Chimica Acta., 60: 125–135 (1975).
Pinto et al., Clinica Chimica Acta., 76: 25–34 (1977).
Ji et al., Proc. Natl. Acad. Sci. USA, 77: 7167–7170 (1980).
Bogdanove et al., Fed. Proc., 35: 778 (1976).
Hazum, Endocrinology, 109: 1281–1283 (1981).
Hardy, Chemical Abstracts, 81 (1974) #74377x.
Castro Desabbatini, et al., Chemical Abstracts, 85 (1976) #173757k.
Khan et al., Clin. Endocrinol. Metab., 54: 705–710 (1982).
Mercier-Bodard et al., J. Steroid Biochem., 11: 253–259 (1979).
Hunter, Chapter 14 of *Handbook of Experimental Immunology*, D. M. Weir, Ed. (Oxford 1978).
Greenwood et al., Nature, 194: 495–496 (1962).
Radioimmunoassay for Human Luterinizing Hormone (HLH), NIAMDD, Revised 2/80.
"Human Prolactin Radioimmunoassay (hPRL RIA)", NIAMDD, 2/18/81.
"Radioimmunoassay for Follicle Stimulating Hormone (HFSH)", NIAMDD, Revised 4/3/80.

*Primary Examiner*—Christine M. Nucker
*Attorney, Agent, or Firm*—Morgan, Finnegan, Pine, Foley & Lee

[57] ABSTRACT

This invention relates to a highly-sensitive mini-iodinated radioactive hormone tracer which has both initial low iodine-to-hormone molar ratios and low specific activity. This invention also relates to methods for preparing and using such tracers in a radio-immunoassay which takes much less time than used heretofore and to a method of preparing said tracers.

23 Claims, 8 Drawing Figures

MINI-IODINATED POLYPEPTIDE HORMONE TRACER AND METHOD FOR ITS USE

BACKGROUND OF THE INVENTION

This invention relates to an improved radioactive tracer which may be used in the assay of chemicals in the body such as polypeptide hormones and drugs and to methods for its preparation and use. More particularly, this invention relates to iodinated polypeptide hormone tracers which have increased sensitivity in assays, longer shelf-life and a generally improved performance during assays although their specific activities are much lower than those of tracers used heretofore. These tracers may be used in a variety of assays, including radioimmunoassays (hereafter referred to as "RIA").

The assays in which the tracers of this invention may be employed are useful for measuring the concentration of a particular substance in blood plasma, for example. For example, the assay can be used as a diagnostic test for a deficiency or overabundance of a hormone in the human body. The assay measures the blood level of the hormone and this level can be compared to the amount considered within normal bounds for individuals of similar physical characteristics. The RIA is based on the binding of antibodies to antigens, or proteins. Many antibodies are manufactured to bind to specific antigens.

The classic method for labelling polypeptide hormones, developed by Hunter and Greenwood, was originally described in Nature, Vol. 194:495 (May, 1962). Hunter and Greenwood suggest that their good results were in part, a consequence of using a low degree of iodination combined with a high specific activity.

"Specific activity" measures the amount of radioactive iodine bound to the protein which is to be used as a tracer. It has been thought that high specific activity, i.e., a high ratio of the amount of bound iodine to the amount of protein (also referred to as "antigen" or "hormone" hereafter), to which it is bound, is desirable for an accurate tracer.

The classic method for preparing tracers suitable for use in RIA is found in "A Radio-immunoelectrophoretic Assay for Human Growth Hormone," Biochemistry J. 91:43, 1964 (Hunter and Greenwood). Hunter and Greenwood employed radioactive $I^{131}$ to label human growth hormone (HGH) for use in RIA. Hunter and Greenwood prepared a tracer having very high specific activity, 250–590 microcuries per microgram (uci/ug). Hunter has indicated that tracers with lower specific activities (i.e. 20–30 uci/ug) are not useful in RIAs, being badly damaged (Hunter, "the Preparation and Assessment of Iodinated 15 Antigens," *Radioimmunoassy Methods*, Kirkham and Hunter, 1971, p. 16).

In order to achieve the desired specific activity, a certain amount of radioactive iodine must be reacted with antigen in the initial reaction. The molar ratio of radioactive iodine to antigen will hereinafter be referred to as the "initial molar ratio." This initial ratio may also be described in terms of the ratios of absolute weights of radioactive iodine to antigen. Hunter and Greenwood used an initial weight ratio of 0.4 mci/ug protein.

It has been suggested that a high degree of iodination may deform the antigen used as a tracer, causing it to react with the antibodies to be used in the assay in a different way from unlabelled antigen, thus negatively affecting the test results. It has, therefore, been recommended that the labelled species be monoiodinated, i.e., have only one radioactive iodine atom per molecule of antigen. (J. E. Hamlin, "Radioiodination of Polypeptide Hormones," Hormones in Human Blood. Detection and Assay, Harry N. Antonaides, Ed., Harvard U.Press, Cambridge, 1976, p. 78). Thus, a recommended specific activity would lie in the range of 50 to 200 uci/ug polypeptide if 50% of the hormone in the tracer mixture is to be labelled. Hamlin also suggests using an initial molar iodine-to-hormone ratio of 0.01 to 0.20 if adequate purification can be performed, with a high specific activity (Hamlin, p.81). This preparation would contain predominantly unlabelled, or non-iodinated hormone with a small percentage of desirable monoiodinated component and no higher order derivatives which interfere with the assay.

The methods for preparing and using these tracers described by Hunter and Greenwood are time consuming. The incubation period required for the antibody-antigen reaction is prolonged due to the nature of antibody-antigen reactions.

RIA procedures performed heretofore required relatively high specific activities and, therefore, exposure to larger amounts of radiation. Exposure to radioactive iodine is dangerous because it may be inhaled and taken up by the thyroid gland, thereby causing it damage. It would be desirable to use a tracer, therefore, with smaller amounts of radioactive material. Iodinated antigens used in RIA heretofore required up to two weeks to obtain satisfactory results. In addition, tracers prepared by known classic methods tend to deteriorate quickly (approximately two weeks), necessitating frequent preparation of new tracers for use in RIAs and incurring increased exposure to radiation and great expense.

It is, therefore, an object of this invention to provide a radioactive tracer which requires less radioactive material than those used heretofore.

It is a further object of this invention to provide a radioactive tracer which is less expensive than known tracers.

It is also an object of this invention to provide a radioactive tracer which maintains at a high level its ability to function over a long period of time, using very small amounts of antigen.

It is an object of this invention to provide a rapid method of assaying polypeptide hormones in vitro.

A novel radioactive tracer composition and method for its preparation has now been discovered which has lower levels of radioactivity, is less expensive, maintains its utility over long periods of time and affords a means of determination of polypeptide hormone levels more rapid and accurate than heretofore known.

DESCRIPTION OF THE INVENTION

This invention relates to a radioactive tracer comprising a body chemical, which is the same chemical as that to be assayed, iodinated with $I^{125}$ wherein the initial molar ratio of $I^{125}$ to body chemical is from about 0.0025 to less than 0.01, the initial weight ratio is from about 10 to less than 50 uci/ug, and the specific activity of the tracer is from about 10 to less than 50 uci/ug body chemical, which has a level of immunoactivity sufficient to bind at least 35% of an appropriate antibody immediately after the tracer has been prepared (hereinafter referred to as "maximum amount of counts bound", or bound/total, Bo/T), said level of immunoactivity decreasing by no more than 50%, with a maximum binding of no less than about 30% at all times, over a substantial time period. Due to the minute amounts of radioactive iodine used, the tracers of this invention are referred to as "mini-iodinated" tracers.

This invention also relates to a method of preparing the iodinated tracer of this invention. This method comprises reacting appropriate amounts of chloramine T, sodium metabisulfite with polypeptide hormone and radioactive iodine, said polypeptide hormone and radioactive iodine being in the molar ratio of from about 0.0025 to about 0.01, weight ratio of 10 to about 50 uci/ug and extracting the iodinated tracer with specific activity of 4 to about 50 uci/ug protein from the reaction mixture.

This invention relates, in addition, to a process of using the iodinated tracer of this invention in a radioimmunoassay which comprises adding a specific first antibody to them and allowing incubation time; adding the iodinated tracer to reaction vessels containing known and unknown quantities of body chemical and allowing incubation time; adding a second antibody and allowing incubation time, obtaining a precipitate, centrifuging and decanting the mixture containing the precipitate; determining the radioactivity of the of the unknown samples and comparing the radioactivity to that of the known samples.

DETAILED DESCRIPTION OF THE PREFERRED EMBODIMENT

The radioactive tracer of this invention preferably has an initial molar ratio of radioactive iodine to polypeptide hormone of about 0.0025 to less than 0.01 and weight ratio of 20 to 47 uci/ug. The specific activity, or ratio of $I^{125}$ (in uci) to ug of iodinated polypeptide hormone is preferably 20 to 35 uci/ug hormone at the start of the assay.

The immunoactivity, or ability of the tracer to bind the antibody specific to it, of the iodinated tracer is determined with the appropriate dilution of antibody (the antibody specific to the polypeptide hormone, or antigen, being measured) and by measuring the percentage of the total radioactive counts present in the resulting precipitate which have been bound to the antibody. The radioactive counts are measured in a Gamma counter. The iodinated tracer should demonstrate a maximum number of counts bound of at least 35%, but preferably at least 50% of the total number of counts.

Figure 1:
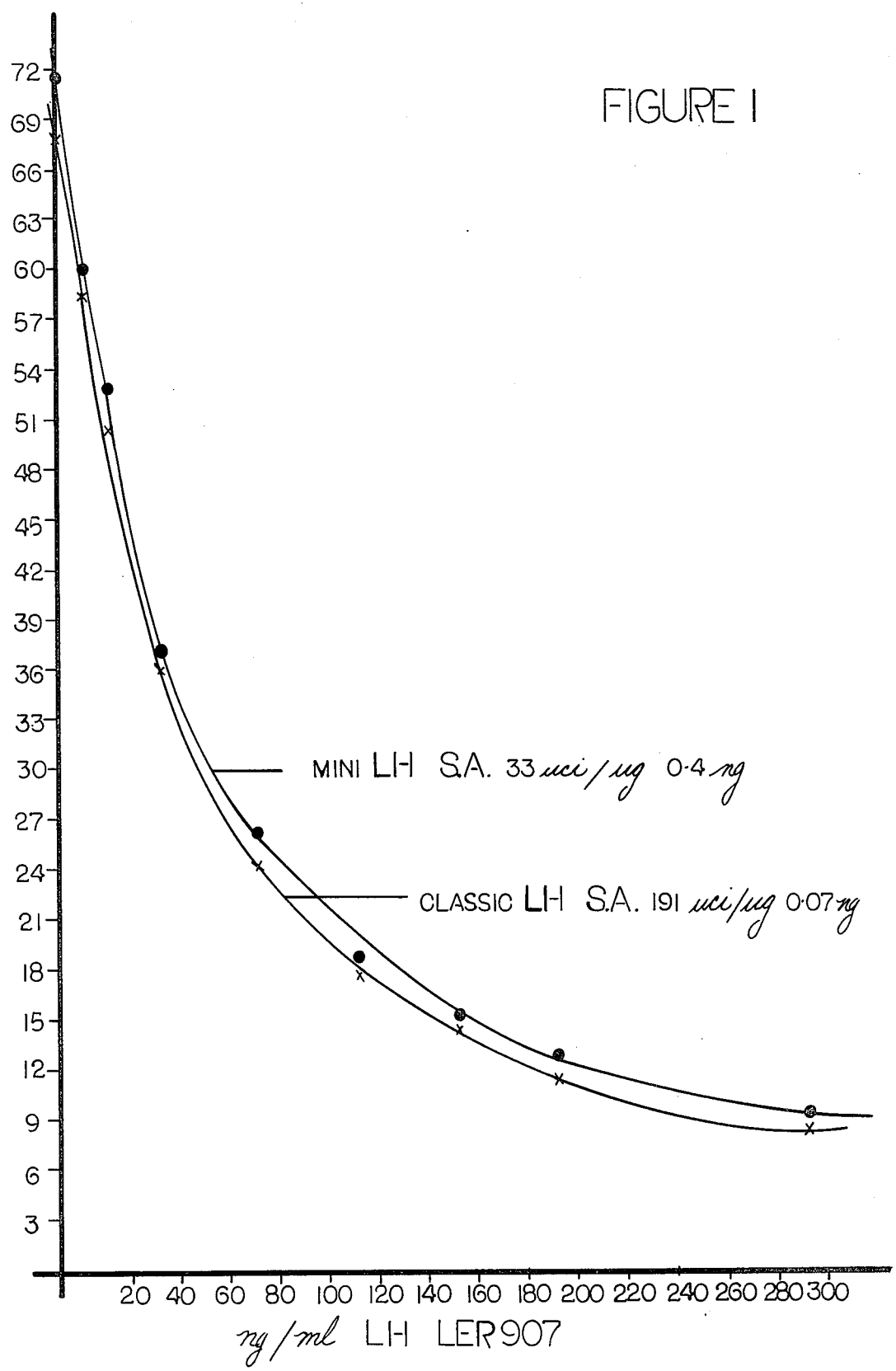
FIGS. 1 and 2 represent Standard Assay curves for Luteinizing Hormone (LH) and Follicle Stimulating Hormone (FSH) respectively.
Figure 2:
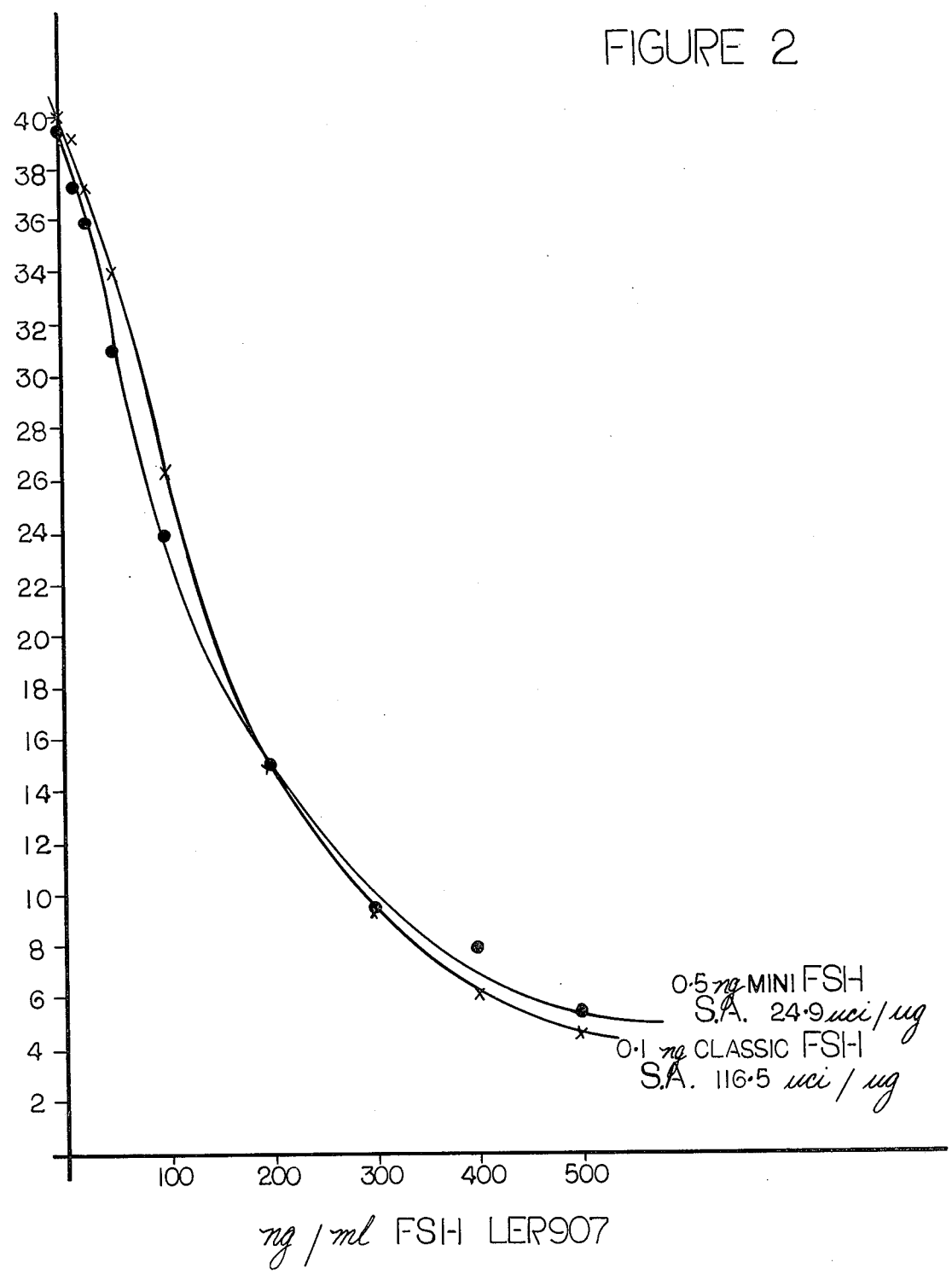
Figure 3:
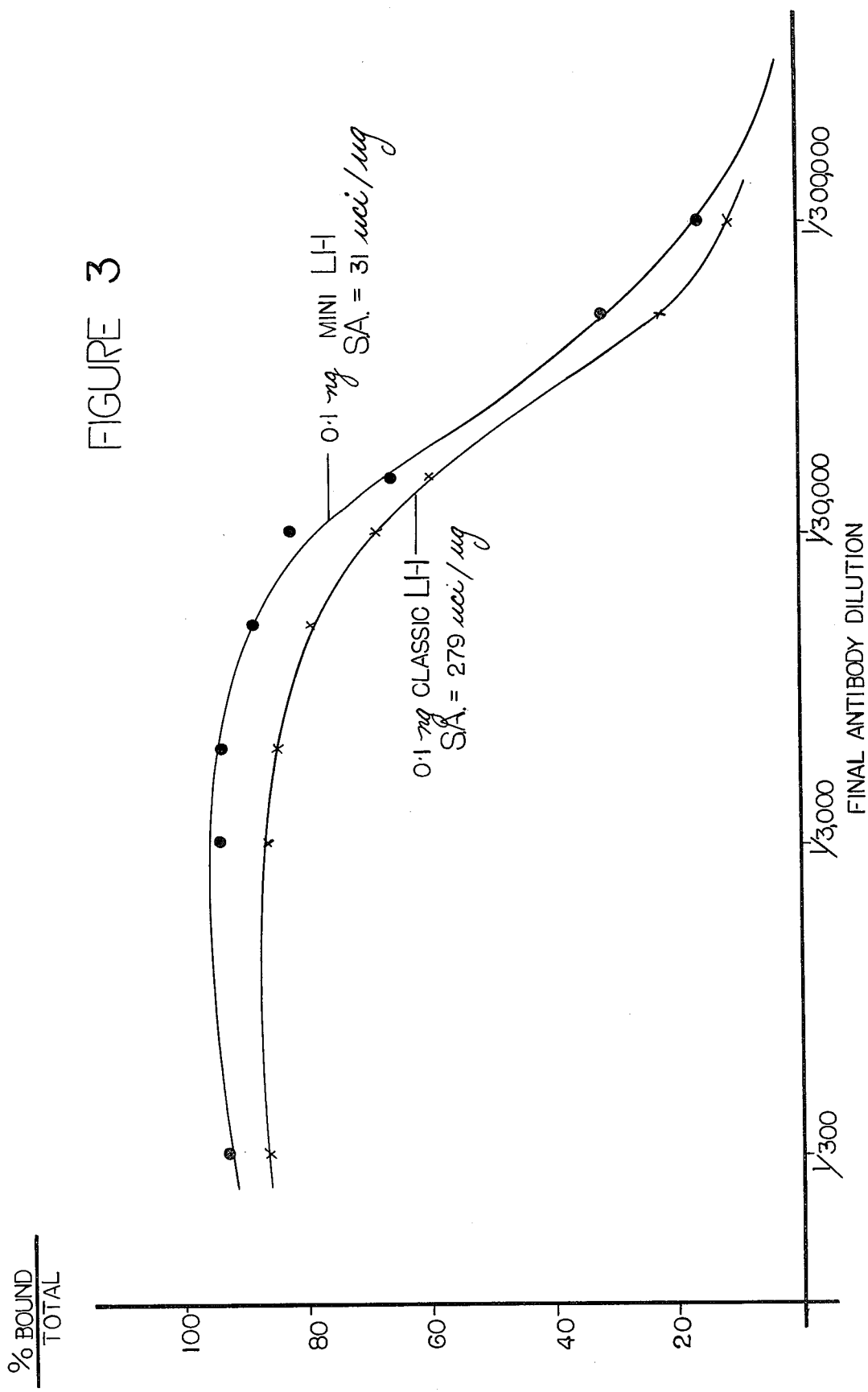
FIGS. 3 and 4 represent Antiserum dilution curves for LH and FSH respectively.
Figure 4:
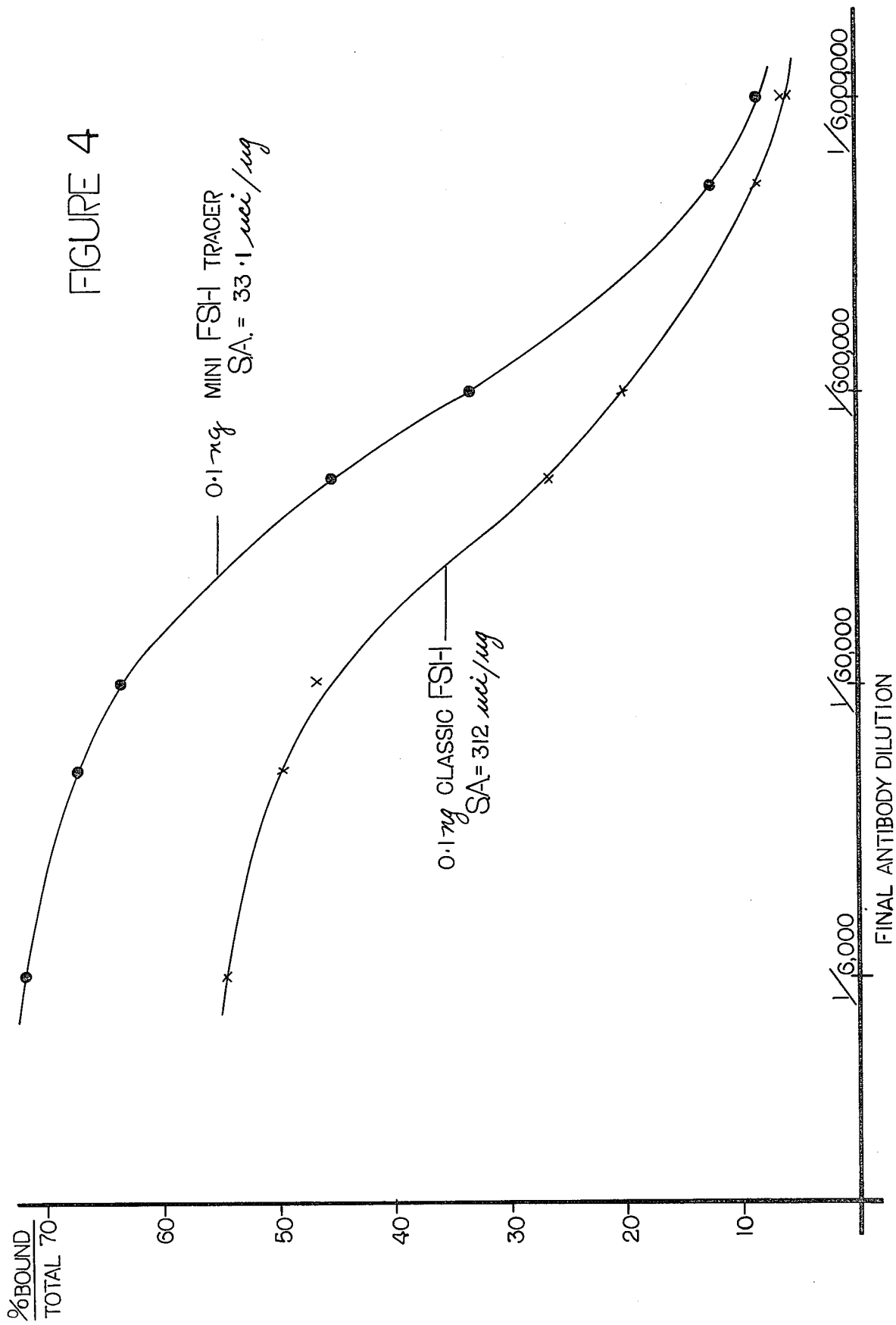

Typical standard curves of the tracer of this invention are represented by FIGS. 1, 2, 3 and 4. FIG. 1 shows both mini-iodinated and classically-iodinated samples of luteinizing hormone (LH). The mini-iodinated sample has a maximum number of counts bound of 71.5%, compared to the conventional maximum of 67.5%. FIG. 2 shows mini-iodinated and classically-iodinated samples of follicle stimulating hormone (FSH) in contrast with a conventionally iodinated sample. The mini-iodinated sample has a maximum number of counts bound of 39.5%; the conventional sample having a maximum of 40%. Thus, tracers of this invention unexpectedly show the same and/or better standard curves as the classic tracers, at a much lower specific activity. The immunoactivity of a tracer described above may be determined by its degree of binding with antigen in different dilutions of the appropriate antibody. In FIGS. 3 and 4, using an equivalent mass of tracer, antiserum dilution curves show an increased binding with the miniiodinated tracer at every dilution tested. FIG. 3 illustrates LH dilution curves and FIG. 4 represents FSH dilution curves.

Figure 5:
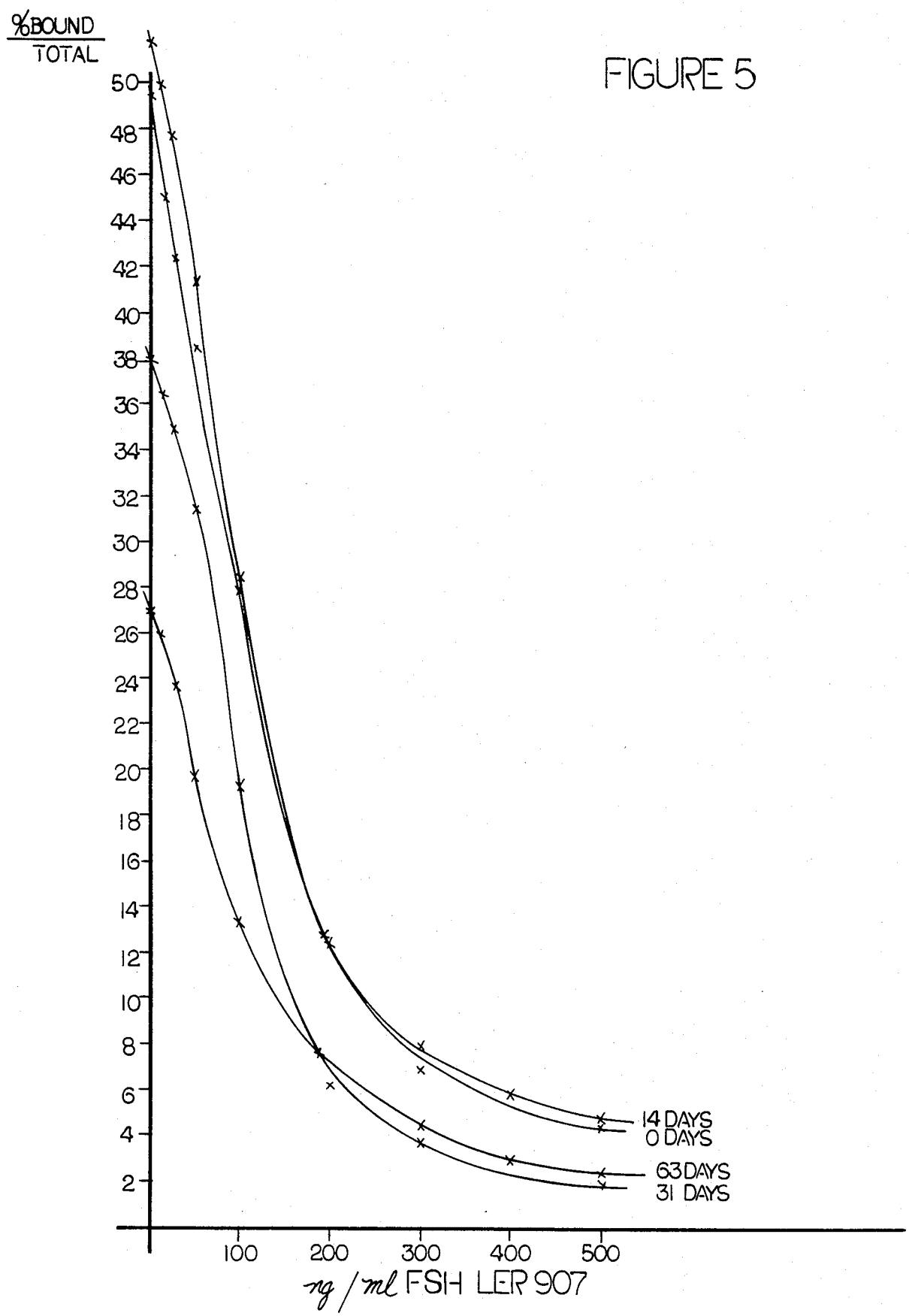
FIGS. 5 and 6 represent Assay curves performed at 0, 14, 31 and 63 days after preparation for mini-iodinated FSH and classically-iodinated FSH respectively.
Figure 6:
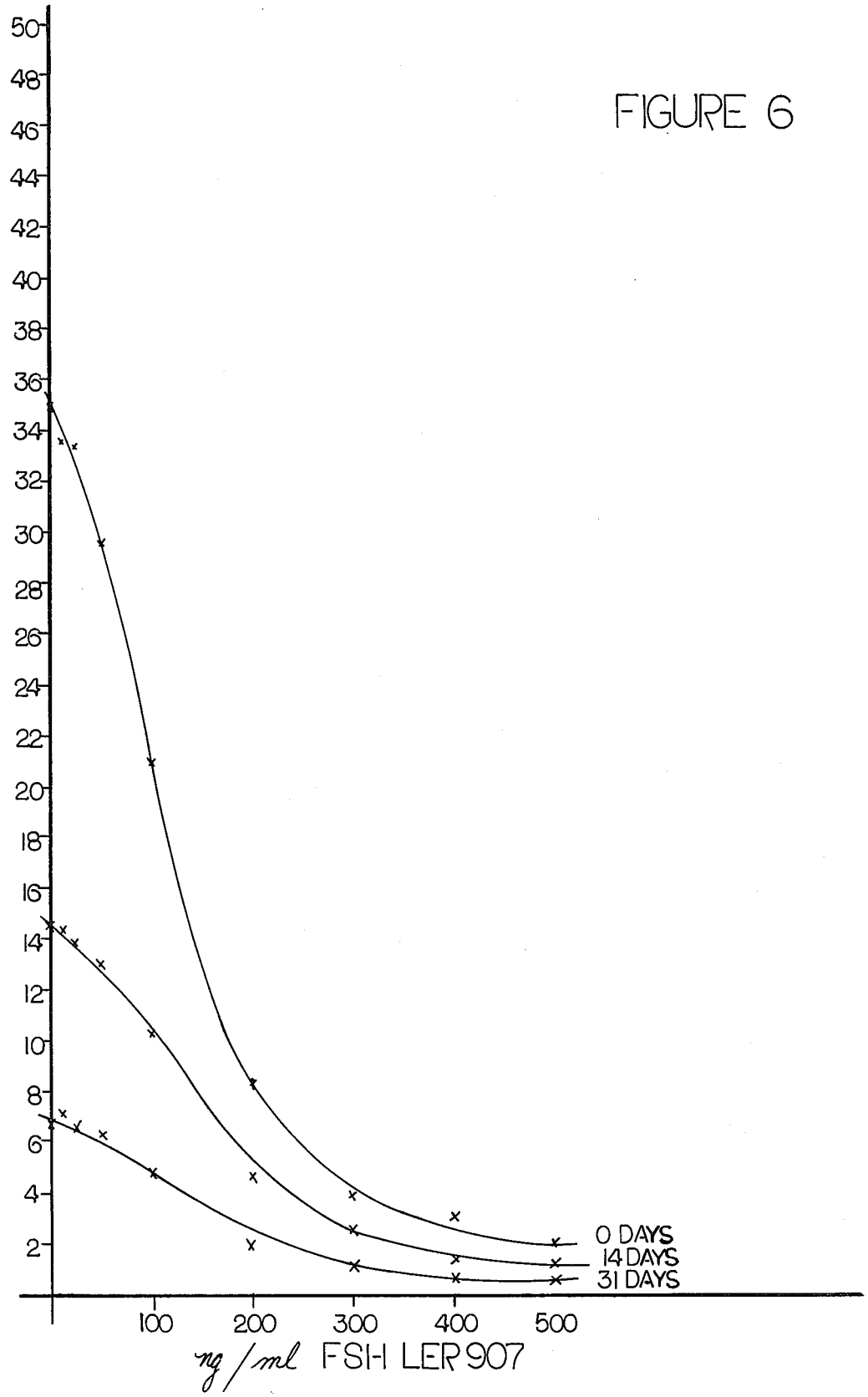
Figure 7:
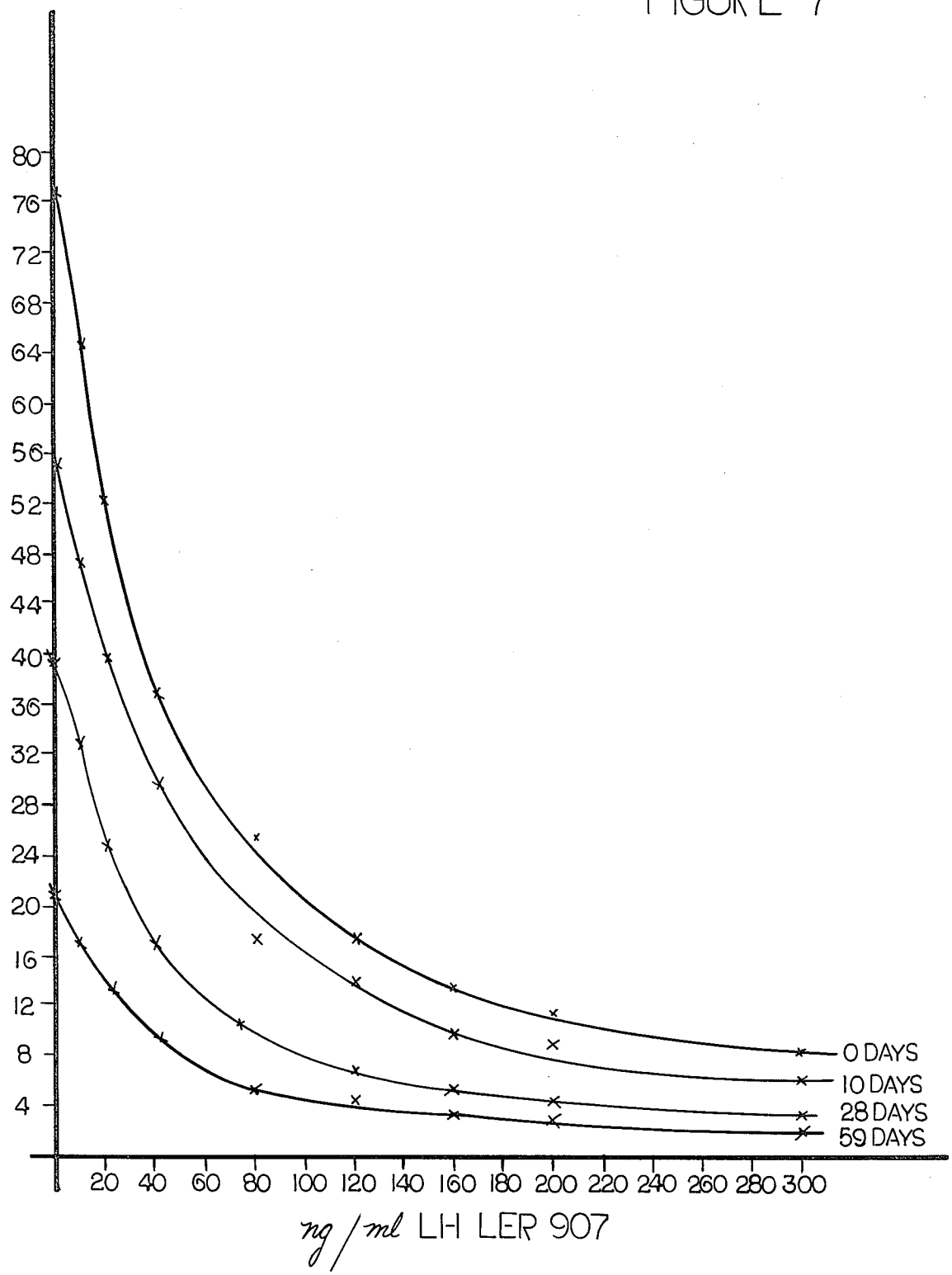
FIGS. 7 and 8 represent Assay curves performed at 0, 10, 28, and 59 days after preparation for classically-iodinated LH and mini-iodinated LH respectively.
Figure 8:
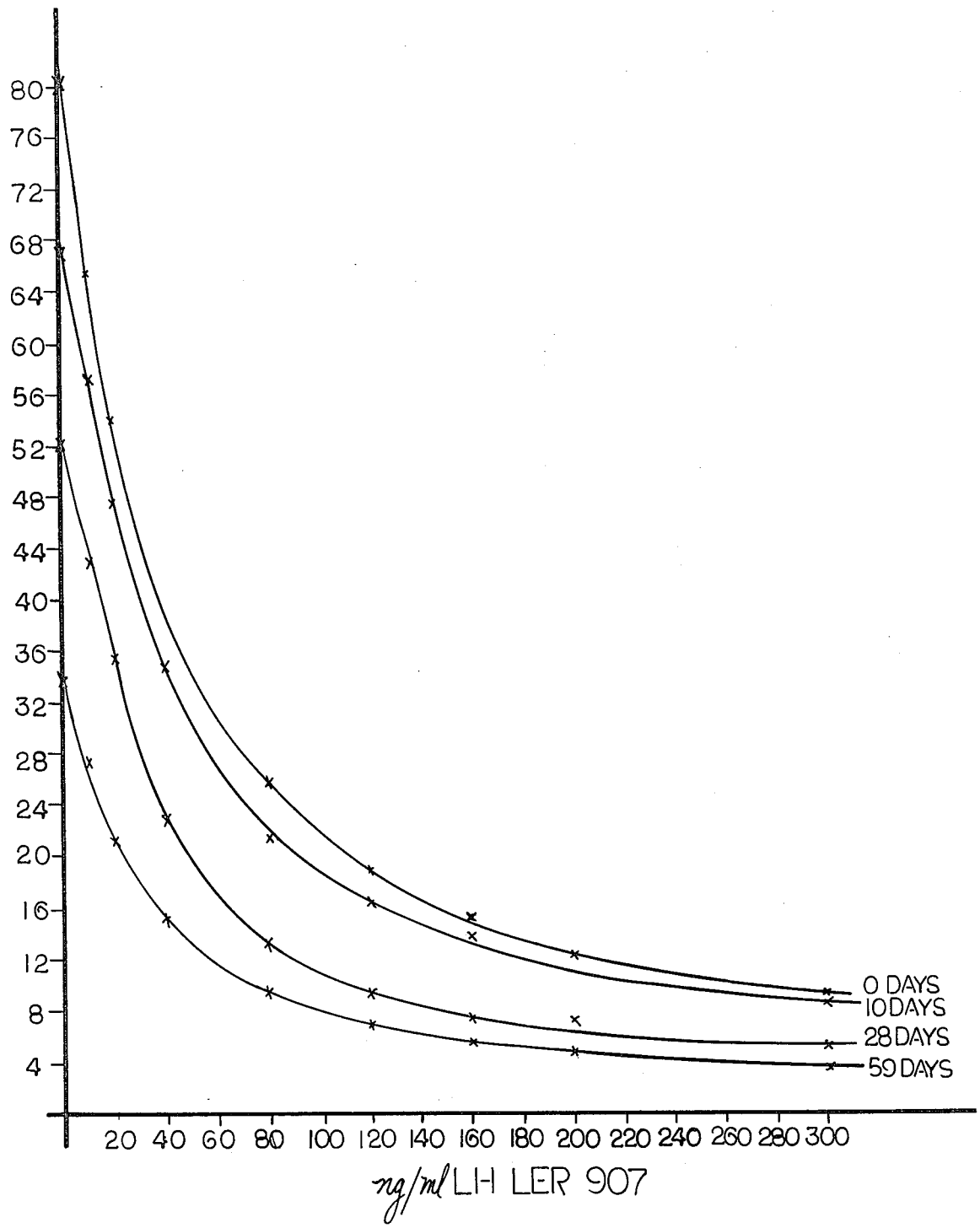

The immunoactivity of tracers iodinated in accordance with this invention preferably decreases not more than 20% over a substantial period of time. This period of time can range from four to eight weeks. Table I shows that mini-iodinated tracers diminish less in immunoactivity than conventionally-iodinated tracers over time. FIGS. 5, 6, 7 and 8 also illustrate this attribute of the mini-iodinated tracers of this inventions. FIGS. 5 and 8 show standard curves plotted over a period of 63 and 59 days, respectively, using mini-iodinated tracers. These figures show that the standard curves do not change dramatically in predominant shape over time as compared to FIGS. 6 and 7, which represent classically-iodinated FSH and LH tracers, respectively.

TABLE I

| Polypeptide | $125_I$ Used | S.A.* uci/ug | Bo/T (%)** Day 0 | Day 30 | CV (%)*** |
|---|---|---|---|---|---|
| FSH | 1.0 mci | 116–312 | 35 | 7 | 10–22 |
| FSH | 0.1 mci | 4–47 | 52 | 38 | 9–14 |
| LH | 1.0 mci | 125–391 | 58 | 17 | 9–18 |
| LH | 0.1 mci | 4–33 | 40 | 37 | 6–13 |

*S.A. represents Specific Activity
Bo/T (%)** represents the maximum percentage of radioactive counts bound.
***CV represents the coefficient of variation of unknown plasma samples read off the standard curve.

Not only does the immunoactivity of the mini-iodinated tracers of this invention diminish less over the course of time than that of classically-iodinated tracers, but the rate at which the immunoactivity decreases is much lower. Table II represents the results of a study of the decrease in binding of $I^{125}$ and labelled protein over time of tracers with different specific activities. The data shows that the rate of the decrease is much greater in high-specific activity, classic tracers than in the mini-iodinated tracers of this invention, i.e. the slope of the classic-tracer line is greater than that of the mini-iodinated tracer line.

TABLE II

| Labelled Protein | Specific Activity (uci/ug) | Drop in Initial Binding (Bo/T %) | |
|---|---|---|---|
| | | After 2 weeks | After 4 weeks |
| LH | 391 | 30.1 | 43.7 |
| | 279 | 23.4 | 40.0 |
| | 191 | 26.8 | 38.1 |
| | 168 | 37.1 | 45.0 |
| | 50 | 18.9 | 24.7 |
| | 33 | 17.6 | 28.2 |
| | 31 | 10.5 | 18.2 |
| | 24.4 | 13.9 | 13.8 |
| | 16.5 | 4.6 | 9.9 |
| Correlation Coefficient($r^2$) | | $r^2 = 0.52$ | $r^2 = 0.69$ |
| FSH | 312 | 24.1 | 33.3 |

TABLE II-continued

| Labelled Protein | Specific Activity (uci/ug) | Drop in Initial Binding (Bo/T %) | |
|---|---|---|---|
| | | After 2 weeks | After 4 weeks |
| | 269 | 19.8 | 28.0 |
| | 239 | 19.1 | * |
| | 160 | 16.7 | 23.9 |

TABLE III

Statistical Results on Control Plasmas
Coefficients of Variation (%)

| | | Intra-Assay | | | | | | Inter-Assay | | | | | |
|---|---|---|---|---|---|---|---|---|---|---|---|---|---|
| | | 4° C. | | | Room Temperature | | | 4° C. | | | Room Temperature | | |
| Tracer | B/Bo | 0 Days | 28 Days | 56 Days | 0 Days | 28 Days | 56 Days | 0 Days | 28 Days | 56 Days | 0 Days | 28 Days | 56 Days |
| Classic | ~90 | 13.7 | —[a] | — | 11.2 | — | — | 22.1 | — | — | 15.3 | — | — |
| FSH | ~82 | 8.1 | — | — | 9.5 | — | — | 13.1 | — | — | 12.2 | — | — |
| (1.0 mci) | ~58 | 8.4 | — | — | 3.0 | — | — | 9.8 | — | — | 8.0 | — | — |
| Mini-FSH | ~90 | 8.5 | 10.6 | 13.2 | 9.6 | 8.7 | 6.4 | 14.3 | 25.3 | 5.1 | 12.9 | 13.4 | 7.1 |
| (0.1 mci) | ~82 | 4.6 | 9.6 | 9.1 | 8.0 | 9.4 | 5.6 | 11.7 | 16.9 | 4.2 | 11.3 | 11.9 | 10.2 |
| | ~58 | 8.5 | 5.2 | 5.1 | 3.0 | 3.8 | 3.9 | 8.7 | 8.7 | 6.0 | 2.5 | 7.9 | 4.4 |
| Classic | ~85 | 11.1 | — | — | 10.3 | — | — | 17.5 | — | — | 17.7 | — | — |
| LH | ~60 | 4.9 | — | — | 5.0 | — | — | 8.8 | — | — | 9.8 | — | — |
| (1.0 mci) | ~35 | 7.6 | — | — | 8.4 | — | — | 12.0 | — | — | 8.3 | — | — |
| Mini-LH | ~85 | 8.4 | 9.6 | 13.5 | 10.8 | 8.0 | 15.5 | 13.1 | 26.9 | 6.7 | 18.1 | 18.5 | 10.5 |
| (0.1 mci) | ~60 | 5.3 | 6.5 | 6.1 | 6.2 | 6.6 | 11.6 | 6.3 | 7.3 | 14.5 | 6.9 | 11.4 | 11.3 |
| | ~35 | 4.3 | 5.9 | 7.8 | 9.5 | 4.3 | 7.2 | 11.6 | 18.0 | 6.4 | 11.1 | 10.0 | 9.2 |

[a]There was an insufficient initial Bo/T to complete the assay (less than 30%).

| 116.5 | 16.0 | 25.8 |
|---|---|---|
| 47.1 | 4.8 | 10.0 |
| 27.4 | 2.7 | 11.0 |
| 24.9 | 6.6 | 11.2 |
| 20.2 | 6.4 | 9.7 |
| | $r^2 = 0.91$ | $r^2 = 0.89$ |

*not performed

The mini-iodinated tracers perform well in assays using plasma samples. This performance is measured by studying the sensitivity and the reproducibility of the assays. Sensitivity and reproducibility are measured by the coefficients of variation of the results obtained by intra-assay, and the coefficients of variation of the results obtained by inter-assay, respectively. The intra-assay measures the variation in results obtained using plasma samples in the same assay. The inter-assay measures the variation between two or more assays performed on different days. Table III represents statistical results obtained by evaluating both intra-assays and inter-assays using mini-iodinated and classically-iodinated tracers. The data in Table III show that the assays performed with mini-iodinated tracers have lower coefficients of variation over a long time-period. This indicates that they are both sensitive and reproducible. The classically-iodinated tracers, however, manifest a rapid decrease in binding and few assays using them obtained reportable results. Generally, an initial binding percentage (Bo/T) of less than 30% produces unacceptable, insensitive results in plasma assays because such tracers produce flat standard curves with very small, slowly-climbing slopes. Therefore, the high-specific activity classically-iodinated tracers which have rapidly-decreased binding levels become quickly unacceptable for use.

The radioactive tracer of this invention is preferably made according to a procedure wherein the bound tracer is collected in a chromatographic column. A Biogel (spherical polyacrylamide gel) chromatography column is prepared by placing a small glass wool plug in the tip of a 10-ml pipette. The pipette is then filled with Biogel to which has been added Barbital Buffer to the 1-ml mark. When all excess buffer from the Biogel has run out to the top of the Biogel, 1 ml of 5% Bovine Serum Albumin (hereinafter referred to as "BSA") is added and allowed to run through. BSA is added to prevent tracer from sticking to the column. The column is washed with Barbital and closed off at the bottom with rubber tubing and a clamp, and sealed at the top and stored at 4° C. until ready for use.

The reaction mixture is then prepared. Chloramine T (10 ul at a concentration of 2.5 mg/ml PBS) and sodium metabisulfite (100 ul at a concentration of 2.5 mg/ml phosphate buffer solution, PBS) solutions are prepared and loaded into automatic dispensing pipettes. Two automatic dispensing pipettes are also filled with 1% potassium iodide (KI) solution of pH 7.5 in PBS, 200 ul in the first and 600 ul in the second.

To 2–2.5 ug of polypeptide hormone to be labelled is added 25 ul of 0.05M sodium Phosphate Buffer (pH 7.5). Ten ul of $I^{125}$, commercially available, (preferably at a level of 0.1 mCi) is then added. In succession, the chloramine T for 60 seconds, sodium metabisulfite for 30 seconds and KI are added and the solution thoroughly mixed after each addition. Five ul of the reaction mixture is then removed and added to a test tube containing 95 ul of 1% BSA and set aside for later determination of specific activity. The remaining reaction mixture is added to the Biogel column. The reaction tube is then rinsed with 600 ul 1% KI and this is added to the column. Fractions are then collected at different times from the Biogel column in test tubes. The fraction in Test Tube #1 will comprise the reaction mixture and KI rinse. The fraction in Test Tube #2 will predominantly contain 1 ml Barbital Buffer. Test Tubes #3A, 3B, 4A and 4B will contain most of the iodinated tracer which results from the reaction. 0.5 ml of the Barbital Buffer solution from the Biogel column should be collected in the four Test Tubes, each of which should contain 0.5 ml of 5% BSA. Test Tubes #5–#15 should contain 1 ml of Barbital Buffer each. 5-ul aliquots from each fraction are counted for radioactivity and the iodinated peak found. All the protein peak tubes are pooled into a 10-ml graduated cylinder and the volume measured. A 10-ul aliquot of the pool is counted for radioactivity.

A 5-ul aliquot of the reaction mixture which was diluted 20 times is counted. Another 5-ul aliquot is run onto an instant thin layer chromatography strip suspended in saline solution. The free $I^{125}$ will run to the top of the strip and the protein will remain at the origin. The strip is cut in half and each half counted for radioactivity. From this the percentage of the reaction mixture consisting of iodinated protein may be calculated. The specific activity can then be calculated as follows:

| | |
|---|---|
| Counts of iodinated protein (cpm) = (Total counts in reaction tube) × | (% counts bound to protein) |
| Disintegrations per minute = (Counts of iodinated protein) × | (efficiency of counter) |
| uci of iodinated protein = (Disintegrations per minute) ÷ | ($2.22 \times 10^6$ dpm/uci) |
| Specific activity = (uci of iodinated protein) × | (μg protein used) |

The iodinated protein may be stored at −20° C.

The mini-iodinated tracers of this invention may be used in all methods employing the use of radio-iodinated tracers. For example, the tracers may be used with methods based on the precipitation of an antibody/antigen complex using chemicals, immunoelectrophoresis or competitive protein binding methods. In addition, they may be used in radio-receptor assays. One preferred use for the novel radioactivity tracer of this invention is in performing the radioimmunoassay of body chemicals. This method may be applied to all body chemicals such as polypeptide hormones, steroid hormones, proteins, amino acids and immunoglobulins, for example growth hormone, insulin, luteinizing hormone, follicle stimulating hormone, thyroid stimulating hormone, prolactin, chorionic hormone, cortisol, digoxin, thyroxine ($T_4$) triiodothyroxine ($T_3$), folic acid, tobramycin, aldosterone, estradiol, estriol, gentamicin, chorionic gonadotropin HCG-$\beta$ sub-unit, IgE and other immunoglobulins, progesterone, testosterone, ferritin, $\alpha$-fetoprotein, gastrin, PAP, prolactin, thyroid-binding globulin, lutenizing hormone releasing hormone (LHRH), LHRH agonists, LHRH antagonists, cortisole releasing factor, $\beta$-endorphin, and drugs and the like.

The preferred type of RIA is the double-antibody system. In this method, the hormone to be assayed is exposed first to the antibody specific to that hormone, and allowed to react. Then, the antibody-antigen complex is then exposed to a second antibody (an antibody to the first antibody or anti-gammaglobulin). The double antibody method is preferable for separating the antigen-antibody complex formed in the reaction mixture because it is widely applicable to a broad range of RIAs. In addition, it is more sensitive and its results are more reproducible than other RIA methods because there is less nonspecific binding (i.e. binding occurring between the labelled protein and antibody which is not specifically made to bind with the particular protein being assayed). The double antibody method is simpler, and more economical than more cumbersome and time-consuming methods, such as electrophoresis. The second antibody, or anti-globulin can be raised in a variety of animals, such as sheep, goats and ponies, which provide large amounts of serum.

The double antibody method uses two types of antibody. The first is the antibody which is specific to the particular antigen being assayed. This antibody is raised in rabbits by multiple injections of the antigen administered at different sites, repeated at two- to three-week intervals. At intervals thereafter the animals are bled and the sera tested for the ability to bind radioiodinated tracer. When an acceptable level of antibody is detected (i.e. enough to bind a significantly measurable amount of tracer), the rabbit is sacrificed and the sera obtained. The second antibody is obtained by injecting a different animal species (such as goats, sheep, ponies) with rabbit serum and obtaining antibodies to the rabbit serum as described above. The antibody so raised acts as an antibody to all rabbit antibodies as it is an anti-gammglobulin.

In the double-antibody method, a series of standard solutions is prepared using a reference preparation of protein.

These standard solutions are used to prepare a standard curve measuring percent of total counts bound versus concentration of hormone to be assayed (see FIGS. 1 and 2, for example). The standard curve can be used to determine the amount of hormone or protein present in an unknown plasma sample by measuring the percent of counts bound in the assayed unknown sample, locating that number along the vertical axis and locating along the horizontal axis the corresponding concentration of protein which gives that number of counts bound on the standard curve. Depending upon the useful range of the standard curve, or the range where there is a wide separation of binding between different concentrations, different dilutions are made ranging from, for example, 500 ng/ml, to 10 ng/ml. A standard curve is set up in triplicate using 200 ul of each standard. Then, three "O" tubes of 200 ul 1% BSA each, three "Blank" tubes with 300 ul BSA each and three "reference" tubes with 300 ul 1% BSA are set up. The "reference" tubes will eventually contain only iodinated tracer and BSA and will be used to indicate the total number of radioactive counts in the tracer/BSA solution. The "blank" tubes will contain all components of the mixture except the first antibody antigen. They will go through the entire process and contain a precipitate at the end of the process which is counted. These counts are "non-specific" counts which indicate the extent to which the tracer binds with components of the process other than the first antibody. The "O" tubes will contain only tracer, the first antibody and BSA, and no unknown or polypeptide hormone. This will represent the initial binding or "O" point on the standard curve.

To measure unknown amounts of antigen in blood plasma, the unknowns should be centrifuged and set up in duplicate, using 50 ul plasma and 150 ul 1% BSA. The appropriate dilution of the first antibody to use should be previously determined by examining the antibody dilution curves and selecting the dilution resulting in an initial binding of 30–60%. The first antibody is added in 50 ul amounts to the "O" tubes, standards and unknowns, but not to the reference or blank tubes. These solutions are shaken to mix them and incubated overnight at 4° C.

The iodinated tracers are then prepared in 1% BSA. Preferably, they should have 18,000–22,000 cpm/50 ul solution. 50 ul of tracer solution should then be added to all tubes. The tubes should be shaken in order to mix their contents and incubated for four to seven days at 4° C.

The second antibody is titered with varying amounts of NRS/PBS (1.25 to 2.5% NRS) to find the best final dilution, i.e., give the highest percent I125 bound in the "O" tube as well as the best precipitate. The precipitate should be visible and firm. Once the best dilution has been determined, the second antibody /NRS/PBS solution should be made up and delivered in 200 ul amounts to the "O" tubes, blank tubes, standard tubes and unknowns, but not to the reference tubes. These tubes should be covered and shaken and incubated at 4° C. for three days.

After the incubation period has ended, all tubes except the reference tubes are preferably centrifuged for 45 minutes at 3500 RPM at 4° C. The liquid from each tube is aspirated and the precipitates counted for radioactivity. The average counts for each reference, blank, standard and unknown are calculated.

To find the %-Bound figure for each standard and unknown, the following formula is used:

$$\% \text{ Bound} = \frac{(\text{cpm sample} - \text{cpm blank})}{(\text{cpm reference} - \text{cpm blank})} \times 100$$

The standard curve is then plotted, with the known concentration along the abscissa and the %-Bound along the axis. The unknowns can be read directly off the curve and multiplied by four to adjust for the volume used in the assay.

The most preferred method of radioimmunoassay using the radioactive iodinated tracer of this invention is more rapid than the traditional method described immediately above. In the preferred method, after 50 ul of the first antibody is added to the tubes, the tubes are shaken and incubated overnight at room temperature. Then, 50 ul of $I^{125}$ tracer are added, the tubes shaken and incubated at room temperature for from one to three days. 200 ul of the second antibody are added and the solution mixed. The tubes are incubated for from two to four hours at room temperature. The remainder of the procedure is the same as that described above.

The steps of he RIA described above may be performed in any order so long as incubation time is allowed. The following examples serve to illustrate the invention, but do not limit it in any manner.

EXAMPLE 1

Iodination of Protein 17.5g of Biogel P60 was washed four times with distilled water. 0.07M Barbital buffer solution of pH 8.6 was added to the washed Biogel P60 and the composition allowed to sit overnight at 4° C. The composition was then decanted and more buffer solution added.

A Biogel P60 column was then prepared by placing a small glass wool plug in the tip of a 10-ml disposable plastic pipette. The pipette was filled to the 1-ml mark with the Biogel composition and the excess buffer allowed to run out to the top of the Biogel. One ml of 5% Bovine Serum Albumin (BSA) in 0.05M phosphate buffer (pH 7.5) was added and run through the column. The column was washed with 20 ml Barbital. The bottom of the column was closed off with rubber tubing and a clamp and the top of the column sealed. The column was stored at 4° C.

A chloramine T solution was prepared immediately before using by dissolving chloramine T in 0.01M Phosphate Buffer Sodium Chloride (PBS) which had a pH of 7.8. The concentration of the chloramine T solution was 2.5 mg/ml PBS. A sodium metabisulfite solution was similarly prepared in PBS at a concentration of 2.5 mg/ml PBS.

Ten ul of chloramine T solution, 100 ul of sodium metabisulfite solution, 200 ul of 1% potassium iodide in 0.05M Phosphate Buffer (pH 7.5) and 600 ul of 1% potassium iodide were placed in pipette guns. Under a hood, 25 ul of 0.95M Sodium Phosphate Buffer (pH 7.5) was added to 2 ug defrosted FSH. Ten ul $I^{125}$ PBS (0.1 mCi) was added. Ten ul of chloramine T solution was added directly of top of these solutions and the entire mixture gently rotated for one minute. 100 ul of sodium metabisulfite solution was added and the mixture again rotated for 30 seconds. 200 ul of potassium iodide was added and mixed in thoroughly. The total volume of the reaction mixture was 365 ul.

Five ul of the resulting mixture was removed and added to a tube containing 95 ul of 1% BSA and set aside for determining the specific activity. The remaining reaction mixture was added to the Biogel column. The reaction tube was rinsed with 600 ul potassium iodide and added to the Biogel column. Fractions were then collected from the Biogel column in polystyrene test tubes as follows:

Tube #1: reaction mixture plus potassium iodide rinse
Tube #2:1 ml Barbital buffer
Tubes 3A, 3B, 4A, 4B: 0.5 ml Barbital buffer collected into tubes containing 0.5 ml 5% BSA
Tube #5–6:.1 ml Barbital buffer each Next, a 5-ul aliquot of the 1:20 diluted reaction mixture or 1/73 of the total mixture, which contained 135,057 cpm, was run onto a Gelman Instant Thin Layer Chromatography strip suspended in saline solution. Free iodide ran to the top of the strip and protein stayed at the origin. The strip was cut in half and each half measured for radioactivity. The percentage of the reaction mixture which was composed of iodinated protein was calculated by dividing the counts remaining at the origin point by the total counts put on the Gelman Strip. Another 5-ul aliquot of the 1:20 dilution was counted for radioactivity to obtain total counts added to the iodination reaction tube.

The total counts in the reaction tube totaled $197 \times 10^6$ cpm. The counts remaining at the origin totaled 74,596 cpm. The counts in the iodide portion of the strip totaled 35,615. The total counts applied to the strip totaled 110,211. Thus, 67.68% of the $I^{125}$ was bound to FSH.

Five-ul aliquots from each fraction of the Biogel column were counted. The iodinated protein peak was in #3A, 3B, 4A, 4B and 5. The peak tubes were pooled in a 10-ml graduated cylinder and the volume measured. A 10-ul aliquot was counted. (See Table 2). Specific activity was calculated from the radioactivity of the iodinated protein measured on the Gelman strip by multiplying the total counts in the reaction tube by 67.68% to find counts bound to FSH. The counts bound to FSH can be ultimately converted to uci/ug by first finding the equivalent number of disintegrations per minute (dpm). The dpm is equal to the counts per minute divided by the efficiency of the counter (63%), or 210,164,000 dpm. One uci equals $2.22 \times 10^6$ dpm, or 94.67 uci. The $I^{125}$ was bound to 2 ug FSH, therefore the specific activity is 47.3 uci/ug FSH.

TABLE IV

| | Radioactivity (cpm) of Fractions Drawn from Column | | | |
|---|---|---|---|---|
| | Example 1 (mini-FSH) | Example 2 (classic FSH) | Example 3 (mini-LH) | Example 4 (classic LH) |
| Fraction # | | | | |
| 1 | 60.0 | 100.0 | 110.0 | 130.0 |
| 2 | 110.0 | 160.0 | 130.0 | 1,485.0 |
| 3a | 49,568.0 | 134,080.0 | 29,850.0 | 384,310.0 |

TABLE IV-continued

| Radioactivity (cpm) of Fractions Drawn from Column | | | | |
|---|---|---|---|---|
| | Example 1 (mini-FSH) | Example 2 (classic FSH) | Example 3 (mini-LH) | Example 4 (classic LH) |
| 3b | 306,183 | —* | 193,469.0 | —* |
| 4a | 117,838.0 | 839,882.0 | 104,869.0 | 816,698.0 |
| 4b | 42,593.0 | 424,715.0 | 32,906.0 | 394,840.0 |
| 5 | 12,749.0 | 159,155.0 | 21,274.0 | 154,461.0 |
| 6 | 13,613.0 | 87,644.0 | 17,714.0 | 137,229.0 |
| counts in 10-ul aliquot | 159,936 | 906,209 | 126,608 | 952,711 |
| Total counts | $102 \times 10^6$ | $580 \times 10^6$ | $82 \times 10^6$ | $610 \times 10^6$ |
| Specific Activity (uci/ug) | 47.3 | 239 | 31 | 279 |

*over 1 million ($1 \times 10^6$) cpm.

EXAMPLE 2

A classic FSH iodination was run using 1 mci of $I^{125}$ instead of 0.1 mci. The results of this Example appear in the Table 4.

EXAMPLE 3

A LH mini-iodination was performed using 0.1 mci of $I^{125}$. The results of this Example appear in Table 4.

EXAMPLE 4

A classic LH iodination was performed using 1 mci of $I^{125}$. The results of this Example appear in Table 4.

EXAMPLE 5

Plasma radioimmunoassay of Luteinizing Hormone

Standard solutions of LER 907 were prepared in the following concentrations from 1:20 diluted stock:

| 0.4 ml + 0.6 ml 1% BSA (2000 ng/ml) | | |
|---|---|---|
| ng/ml | ml Std. | ml 1% BSA |
| 300 | 0.15 | 0.85 |
| 200 | 0.4 | 3.6 |
| 160 | 0.8 | 0.2 |
| 120 | 0.6 | 0.4 |
| 80 | 0.4 | 0.6 |
| 40 | 0.2 | 0.8 |
| 20 | 0.1 | 0.9 |
| 10 | 0.05 | 0.95 |

11×75 mm polystyrene test tubes were set up to establish a standard curve and to measure unknowns. Each standard sample, including a zero-point sample comprising 200 ul of 1% BSA, was made up in triplicate using 200 ul of each standard. Three blank tubes with 300 ul 1% BSA and three reference tubes with 300 ul 1% BSA were also made up. Unknowns were set up in duplicate using 50 ul plasma and 150 ml 1% BSA.

An automatic dispensing pipette was used to dispense 50 ul of Rabbit anti-LH (titered to the best dilution which gives a "O" point of 40–50% binding, or 1:4,000 LH) into all tubes except the reference and blank tubes. These were covered, shaken and mixed, and incubated overnight at 4° C.

$I^{125}$ tracers were prepared in 1% BSA which had a count of 18,000–22,000 cpm/50 ul. 50 ul of tracer was added to all tubes. They were covered, mixed and incubated at 4° C. for four-seven days.

The second antibody (normal rabbit serum used as 1.25%–2.5% in PBS with antirabbit gamma-globulin titered to give the highest percent-bound in the "O" tube along with the best precipitate, which is visible and firm). 200 ul was added to all tubes except reference tubes. The tubes were covered, shaken and incubated at 4° C. for 3 days.

After three days, all tubes except the reference tubes were centrifuged for 45 minutes at 3500 RPM at 4° C.

The liquid was aspirated from each tube and the precipitates counted. The average counts for each reference, blank, standard and unknown were calculated. The results of this example appear in Table 5.

TABLE V

| Radioimmunoassay - Standard Curve Data for Mini-iodinated Luteinizing Hormone | | | | |
|---|---|---|---|---|
| Dilution | Cpm | Avg. | B/T | Avg. B/T |
| Reference | 17,070.0 | | | |
| | 15,742.0 | 16,406.0 | | |
| Blank | 407.0 | | | |
| | 487.0 | 447.0 | | |
| Standards* (ng/ml) | | | | |
| 0.0 | 11,347.0 | | 68.30% | 68.14% |
| 0.0 | 11,295.5 | | 67.98% | |
| 10.0 | 9,126.0 | | 54.38% | 53.16% |
| 10.0 | 8,737.0 | | 51.95% | |
| 20.0 | 7,940.5 | | 46.95% | 46.74% |
| 20.0 | 7,893.5 | | 46.53% | |
| 40.0 | 5,958.0 | | 34.53% | 33.69% |
| 40.0 | 5,690.0 | | 32.85% | |
| 80.0 | 4,221.5 | | 23.65% | 23.27% |
| 80.0 | 4,099.0 | | 22.88% | |
| 120.0 | 3,154.5 | | 16.99% | 16.98% |
| 120.0 | 3,159.0 | | 16.99% | |
| 160.0 | 2,871.5 | | 15.19% | 14.95% |
| 160.0 | 2,794.0 | | 14.71% | |
| 200.0 | 2,413.5 | | 12.32% | 12.16% |
| 200.0 | 2,363.0 | | 12.01% | |
| 300.0 | 2,042.5 | | 10.00% | 10.13% |
| 300.0 | 2,085.5 | | 10.27% | |
| Unknowns* (sample no.) | | | | Found Concn. (Ng/ml) |
| 1 | 9,860.0 | | 59.02% | 24 |
| 1 | 9,680.0 | | 57.89% | 28 |
| 2 | 7,195.0 | | 42.28% | 96 |
| 2 | 6,884.0 | | 40.36% | 112 |
| 3 | 4,057.0 | | 22.58% | 336 |
| 3 | 4,186.0 | | 23.40% | 316 |

*The unknown plasma results have been multiplied by four to adjust for the volume used in the assay.

EXAMPLE 6

Rapid Radioimmunoassay Method

Same procedure was performed as in Example II until the addition of the first antibody. The first antibody was added to the appropriate tubes, the tubes covered, shaken and incubated overnight at room temperature. The tracer was then added, the contents of the tubes again mixed and incubated at room temperature for one to three days. The second antibody was then added and the tubes incubated for two to four hours at room temperature. The remainder of the procedure follows that of Example 5. The standard curve data performed with LH and FSH appear in Tables 6 and 7.

TABLE VI

| Rapid Radioimmunoassay - Standard Curve Data for Mini-iodinated Luteinizing Hormone | | | | |
|---|---|---|---|---|
| Dilution | Cpm | Avg. | B/T | Avg. B/T |
| Reference | 18,137.0 | | | |
| | 17,619.0 | 17878.0 | | |
| Blank | 444.0 | | | |

TABLE VI-continued

Rapid Radioimmunoassay - Standard Curve Data for Mini-iodinated Luteinizing Hormone

| Dilution | Cpm | Avg. | B/T | Avg. B/T |
|---|---|---|---|---|
| | 469.0 | 456.0 | | |
| Standards* (ng/ml) | | | | |
| 0.0 | 11,781.0 | | 65.00% | 64.70% |
| 0.0 | 11,674.0 | | 64.39% | |
| 10.0 | 8,855.0 | | 48.21% | 48.84% |
| 10.0 | 9,074.0 | | 49.46% | |
| 20.0 | 7,278.0 | | 39.16% | 39.10% |
| 20.0 | 7,259.0 | | 39.05% | |
| 40.0 | 5,414.0 | | 28.46% | 27.34% |
| 40.0 | 5,025.0 | | 26.22% | |
| 80.0 | 3,672.0 | | 18.46% | 18.61% |
| 80.0 | 3,725.0 | | 18.76% | |
| 120.0 | 2,975.0 | | 14.46% | 13.99% |
| 120.0 | 2,806.0 | | 13.49% | |
| 160.0 | 2,572.0 | | 12.14% | 11.81% |
| 160.0 | 2,455.0 | | 11.47% | |
| 200.0 | 2,272.0 | | 10.42% | 10.21% |
| 200.0 | 2,197.0 | | 9.99% | |
| 300.0 | 1,772.0 | | 7.55% | 7.55% |
| 300.0 | 1,771.0 | | 7.55% | |
| Unknowns* (sample no.) | | | | Found Concn. (Ng/ml) |
| 1 | 10,130.0 | | 55.53% | 24 |
| 1 | 10,330.0 | | 56.67% | 20 |
| 2 | 6,415.0 | | 34.20% | 104 |
| 2 | 6,234.0 | | 33.16% | 112 |
| 3 | 3,907.0 | | 17.80% | 286 |
| 3 | 3,806.0 | | 17.23% | 300 |

*The unknown plasma results have been multiplied by four to adjust for the volume used in the assay.

TABLE VII

Rapid Radioimmunoassay - Standard Curve Data for Mini-iodinated Follicle Stimulating Hormone

| Dilution | Cpm | Avg. | Bo/T | Avg. Bo/T |
|---|---|---|---|---|
| Reference | 18,533.0 | | | |
| | 17,873.0 | 18,203.0 | | |
| Blank | 443.0 | | | |
| | 388.0 | 415.5 | | |
| Standards* (ng/ml) | | | | |
| 0.0 | 8,893.0 | | 47.66% | |
| 0.0 | 9,003.0 | | 48.28% | 47.97% |
| 50.0 | 8,607.0 | | 46.05% | |
| 50.0 | 8,487.0 | | 45.38% | 45.71% |
| 100.0 | 8,403.0 | | 44.91% | |
| 100.0 | 8,428.0 | | 45.05% | 44.98% |
| 200.0 | 6,927.0 | | 36.61% | |
| 200.0 | 7,195.0 | | 38.11% | 37.36% |
| 400.0 | 5,069.0 | | 26.16% | |
| 400.0 | 4,895.0 | | 25.18% | 25.67% |
| 800.0 | 2,487.0 | | 11.65% | |
| 800.0 | 2,386.0 | | 11.08% | 11.36% |
| 1200.0 | 1,646.0 | | 6.92% | |
| 1200.0 | 1,660.0 | | 7.00% | 6.96% |
| 1600.0 | 1,300.0 | | 5.53% | 5.25% |
| 1600.0 | 1,399.0 | | 5.53% | 5.25% |
| 2000.0 | 1,141.0 | | 4.08% | |
| 2000.0 | 1,185.0 | | 4.33% | 4.20% |
| Unknowns* (sample no.) | | | | Found Concn. (Ng/ml) |
| 1 | 7,924.0 | | 42.21% | 124 |
| 1 | 7,850.0 | | 41.80% | 132 |
| 2 | 6,722.0 | | 35.45% | 232 |
| 2 | 6,877.0 | | 36.33% | 220 |
| 3 | 3,588.0 | | 17.84% | 544 |
| 3 | 3,765.0 | | 18.83% | 520 |

*The unknown plasma results have been multiplied by four to adjust for the volume used in the assay.

What is claimed is:

1. A radioactive tracer produced by a process comprising reacting a body chemical and radioactive iodine in the presence of chloramine-T and sodium metabisulfite; wherein the initial molar ratio of radioactive iodine to body chemical is from about 0.0025 to less than 0.01; the initial weight ratio is from about 10 uci/ug to less than 50 uci/ug; said tracer having a level of immunoactivity sufficient to bind at least 35% of an appropriate antibody immediately after the tracer has been prepared, said level of immunoactivity decreasing by no more than 50% with a maximum binding of no less than about 30% at all times, over a substantial time period.

2. A radioactive tracer according to claim 1 wherein the initial molar ratio is between 0.0025 and 0.009.

3. A radioactive tracer according to claim 1 wherein the initial weight ratio is between about 20 and about 47.

4. A radioactive tracer according to claim 1 wherein the specific activity is between about 20 and about 35.

5. A radioactive tracer according to claim 1 wherein said tracer binds at least about 40% of an appropriate antibody immediately after the tracer has been prepared.

6. A radioactive tracer according to claim 1 wherein the chemical is a polypeptide hormone.

7. A radioactive tracer according to claim 1 wherein the chemical is selected from the group of LH and FSH.

8. A method for preparing a radioactive iodinated tracer which comprises reacting appropriate amounts of chloramine T, sodium metabisulfite with a body chemical and radioactive iodine, said body chemical and radioactive iodine being in the ratio of from about 0.0025 to about 0.01 and initial weight ratio of about 10 to less than 50 uci/ug and extracting the iodinated tracer with specific activity of about 4 to less than 50 uci/ug of body chemical from the reaction mixture.

9. A process for assaying body chemicals with a radioactive tracer as defined in claim 1 which comprises adding a specific first antibody to reaction vessels containing known and unknown quantities of body chemical and allowing incubation time; adding tracer to the incubated mixture and allowing incubation time; adding a second antibody to the twice incubated mixture and allowing incubation time; obtaining a precipitate, centrifuging and decanting the mixture containing the precipitate, determining the radioactivity of the precipitate of the unknown quantities and comparing it to that of the known quantities.

10. A process according to claim 9 wherein the first incubation time after adding the first antibody requires 12 to 24 hours, the incubation time after adding tracer requires one to three days and the incubation time after adding the second antibody requires 2 to 4 hours.

11. A process according to claim 9 wherein the first antibody and the tracer are added simultaneously.

12. A process according to claim 9 wherein the incubation time of the knowns, unknowns, first antibody and tracer requires from 1 to 3 days.

13. A process for assaying body chemicals using a radioactive tracer as defined in claim 1 which comprises adding tracer to vessels containing known and unknown quantities of chemical to be assayed, adding to the vessels a substance which binds the tracer, separating the complex of tracer and substance which binds the tracer and measuring the radioactivity of the complex.

14. A radioactive tracer produced by a process comprising reacting a polypeptide hormone and $I^{125}$ in the presence of chloramine-T and sodium metabisulfite, wherein the initial molar ratio of $I^{125}$ to polypeptide hormone is from about 0.0025 to less than 0.01; the initial weight ratio is from about 10 uci/ug to less than 50 uci/ug, wherein the initial molar ratio of radioactive iodine to body chemical is from about 0.0025 to less than 0.01; the initial weight ratio is from about 10 uci/ug to less than 50 uci/ug; said tracer having a level of immunoactivity sufficient to bind at least 35% of an appropriate antibody immediately after the tracer has been prepared, said level of immunoactivity decreasing by no more than 50% with a maximum binding of no less than about 30% at all times, over a substantial time period.

15. A radioactive tracer according to claim 14 wherein the initial molar ratio is between 0.0025 and 0.009.

16. A radioactive tracer according to claim 14 wherein the initial weight ratio is between about 20 and about 47.

17. A radioactive tracer according to claim 14 wherein the specific activity is between about 20 and about 35.

18. A radioactive tracer according to claim 14 wherein said tracer binds at least about 40% of an appropriate antibody immediately after the tracer has been prepared.

19. A method for preparing a radioactive iodinated tracer which comprises reacting appropriate amounts of chloramine-T and sodium metabisulfite with a polypeptide hormone and radioactive iodine, said polypeptide hormone and radioactive iodine being in the molar ratio of from about 0.0025 to about 0.01 and initial weight ratio of about 10 to less than 50 uci/ug and extracting the iodinated tracer with specific activity of about 4 to less than 50 uci/ug of polypeptide hormone from the reaction mixture.

20. A process for assaying polypeptide hormones with a radioactive tracer as defined in claim 14 which comprises adding a specific first antibody to reaction vessels containing known and unknown quantities of body chemical and allowing incubation time; adding tracer to the incubated mixture and allowing incubation time; adding a second antibody to the twice incubated mixture and allowing incubation time; obtaining a precipitate, centrifuging and decanting the mixture containing the precipitate, determining the radioactivity of the precipitate of the unknown quantities and comparing it to that of the known quantities.

21. A process according to claim 20 wherein the first incubation time after adding the first antibody requires 12 to 24 hours, the incubation time after adding tracer requires one to three days and the incubation time after adding the second antibody requires 2 to 4 hours.

22. A process according to claim 20 wherein the first antibody and the tracer are added simultaneously.

23. A process according to claim 20 wherein the incubation time of the knowns, unknowns, first antibody and tracer requires from 1 to 3 days.

* * * * *

UNITED STATES PATENT AND TRADEMARK OFFICE
CERTIFICATE OF CORRECTION

PATENT NO. : 4,474,891
DATED : October 2, 1984
INVENTOR(S) : Michelle P. Warren, Elsie C. Ewen It is certified that error appears in the above—identified patent and that said Letters Patent is hereby corrected as shown below:

Column 7, line 12, delete "X" and insert therefor -- $\div$ --.

Column 7, line 17, delete "X" and insert therefor -- $\div$ --.

Column 10, line 2, delete "0.95M" and insert therefor --0.05M--.

Signed and Sealed this

Twenty-eighth Day of May 1985

[SEAL]

Attest:

DONALD J. QUIGG

Attesting Officer  Acting Commissioner of Patents and Trademarks